United States Patent [19]

Boucher

[11] Patent Number: 5,219,890
[45] Date of Patent: Jun. 15, 1993

[54] ODORLESS MYCOBACTERICIDAL COMPOSITIONS

[75] Inventor: Raymond M. G. Boucher, Houston, Tex.

[73] Assignee: Wave Energy Systems, Inc., Houston, Tex.

[21] Appl. No.: 809,086

[22] Filed: Dec. 9, 1991

Related U.S. Application Data

[63] Continuation of Ser. No. 378,053, Jul. 11, 1989, abandoned.

[51] Int. Cl.⁵ .................. A61K 31/11; A01N 35/00
[52] U.S. Cl. .................................................. 514/705
[58] Field of Search ........................................ 514/705

[56] References Cited

U.S. PATENT DOCUMENTS

| | | | |
|---|---|---|---|
| 2,801,216 | 7/1957 | Yoder et al. | 424/333 |
| 3,079,985 | 3/1963 | Boehne | 514/694 |
| 3,886,269 | 5/1975 | Trujillo | 514/694 |
| 3,917,850 | 11/1975 | Boucher | 514/694 |
| 3,968,248 | 7/1976 | Boucher | 252/106 |
| 3,968,250 | 7/1976 | Boucher | 514/705 |
| 3,983,252 | 9/1976 | Buchalter | 514/705 |
| 4,048,336 | 9/1977 | Winicov | 514/694 |
| 4,093,744 | 6/1978 | Winicov | 514/694 |
| 4,436,754 | 3/1984 | Jacobs . | |
| 4,590,214 | 5/1986 | Zamore | 514/702 |
| 4,859,186 | 8/1989 | Ranly | 514/694 |
| 4,978,530 | 12/1990 | Strong | 424/413 |

FOREIGN PATENT DOCUMENTS

| | | |
|---|---|---|
| 0046375 | 2/1982 | European Pat. Off. . |
| 0251743 | 1/1988 | European Pat. Off. . |
| 1508847 | 1/1967 | France . |

OTHER PUBLICATIONS

"Official Methods of Analysis", Assn. of Official Analytical Chemists (AOAC), 12th ed., 1975.
Sidwell, R. W., "Potentially Infectious Agents Associated with Shearling Bed Pads", *Applied Microbiology*, Jan. 1970.
S. P. Gorman and E. M. Scott, "Potentiation and Stabilization of Glutaraldehyde Biocidal Activity Utilizing Surfactant—Divalent Cation Combinations," 4 *International Journal of Pharmaceutics*, pp. 57–65 (1979).
"Interférence De Deux Surfactants Anioniques Sur L'Activité Bactéricide De Quelques Antiseptiques", *Journal of Pharmacie De Belqique*, vol. 38, No. 2, 1983, pp. 101–104.
Kabara (Wallhausser) *Cosmetic & Drug Preservation* pp. 649–650.

*Primary Examiner*—S. J. Friedman
*Attorney, Agent, or Firm*—Pravel, Hewitt, Kimball & Kreiger

[57] ABSTRACT

Efficacious phenol-free mycobactericidal liquid compositions having low odor and irritation potential are disclosed. These compositions consist of a solvent containing a glycol, a 2 to 6 carbon atom aldehyde, specific anionic surfactants, and buffer salts to stabilize the pH in the 6 to 7.4 range. The ratio of glycol to aldehyde is comprised between 0.1 and 6.0. The lower this ratio, the greater the mycobactericidal activity. The new odorless compositions can kill *Mycobacterium tuberculosis* (EPA quantitative procedure) in 10 minutes or less at 20° C.

20 Claims, 2 Drawing Sheets

ODORLESS MYCOBACTERICIDAL COMPOSITIONS

This is a continuation of co-pending application Ser. No. 07/378,053 filed on Jul. 11, 1989, now abandoned.

BACKGROUND OF THE INVENTION

Although many glutaraldehyde/surfactant solutions have been evaluated for their sporicidal or bactericidal activity, very few such solutions have been thoroughly investigated from the mycobactericidal activity view point. It is well-known that there is no direct relationship between spores and mycobacteria resistances to chemical disinfectants. For example, while under certain conditions phenols and isopropylalcohol can be extremely potent against *M. tuberculosis*, the same chemicals have always displayed very poor sporicidal activity.

It is also well-known that cells of *M. tuberculosis* are among the most resistant vegetative microorganisms, and after bacterial endospores, these cells constitute the most severe challenge to chemical germicides. However, until recently, the efficacy of glutaraldehyde solutions to quickly destroy *M. tuberculosis* on animate or inanimate surfaces has been questioned by several authors. Rubbo et al (J. Appl. Bact., 30:78-87, 1967) were the first to challenge the tuberculocidal efficacy of 2% alkaline glutaraldehyde solutions sold under the CIDEX trade name (Surgikos, a Johnson and Johnson company). A 1971 study by T. Bergan and A. Lysad relates to the antitubercular action of several types of disinfectants using a method adapted from the Kelsey-Sykes test for disinfectants. It was concluded that the 2% glutaraldehyde solution was not adequately effective, growth occurring after the second incremental addition of bacteria. In November 1976, Boucher et al filed a report at the Environmental Protection Agency on a comparative study of the tuberculocidal efficacy of acid and alkaline glutaraldehyde (2%) compositions. These conclusions, based on hundreds of Association of Official Analytical Chemists (AOAC) tests using more than 4000 test tubes conducted at the Ontario Research Foundation, -found- that 2% alkaline glutaraldehyde did not kill *M. tuberculosis* var *bovis* (BCG) in 10 or even 20 minutes at 20° C. Although tuberculocidal times seemed to be shorter (15 to 20 min) with a potentiated acid glutaraldehyde at pH 3.5, results were not statistically significant. It was noted that the use of different neutralizers (sodium bisulfite or horse serum) provided different results. Following the identical method, slight variations of temperature between 20° C. and 25° C. also gave wide variations in tuberculocidal activity.

In November 1976, FM Collins and V. Montalbine reported (Journ Clin Microb, p. 408-412, Nov. 1976) that 2% alkaline glutaraldehyde solution inactivated $10^5$ viable *M. tuberculosis* H37Rv cells present on the surface of porcelain penicylinders within 3 min. at 18° C. A potentiated acid glutaraldehyde needed five minutes to be tuberculocidal at the same temperature. This method was different from the AOAC procedure (a pass/fail test) and the results were so optimistic that they were skeptically received.

During this period, numerous discrepancies resulting from use of the AOAC method (or procedures derived from it) attracted the attention of many scientists interested in a more accurate methodology. In October 1984, J M Ascenzi, T M Wendt, and J W McDowell in a paper entitled "Important Information Concerning the Reuse of Glutaraldehyde-Based Disinfectants and their Tuberculocidal Activity", first evaluated seven known glutaraldehyde sterilizing compositions with a new quantitative technique said to be very accurate and reproducible. They varied the contact times (1, 2, 5, 10, and 20 minutes) at a standard temperature of 20° C. and none of the disinfectants which were tested showed complete kill of the test populations of mycobacteria in ten or twenty minutes. Table I shows the specific data pertaining to this study. This was extremely important since all of these commercial solutions had been previously approved for 10 and 20 minutes tuberculocidal efficacy with the AOAC method. The Environmental Protection Agency (EPA), having regulation authority over label claims of sterilants and disinfectants, convened a panel of experts in September 1985 to evaluate this new quantitative procedure and to compare it with the old AOAC method. Notwithstanding, the EPA decided that all Registrants/Applicants of all antimicrobial pesticides with existing tuberculocidal claims for fresh or reused solutions would have to retest their products with one of the three following options:

(a) The new quantitative method, (b) the old AOAC method but with substantial modification of the exposure time and temperature, (c) the standard AOAC method using 20° C. and 10 minutes exposure time in a laboratory other than the one which developed the original data.

The tuberculocidal data call-in-notice was issued on Jun. 13, 1986 and the results were released on Feb. 17, 1989. Only 43 products of a total of 144 satisfied the data requirements of the call-in. Among the glutaraldehyde-based products only 60% satisfied the call-in requirements. Only four companies tested their products with the new and more accurate quantitative method. Vast discrepancies exist in comparing the quantitative method with the old AOAC approach. For instance, at 20° C., a standard alkaline solution (CIDEX 2%) needed 70 min. to kill *M. tuberculosis*, the CIDEX formula needed 2 hours and the CIDEX Machine 4 hours. Previously, these solutions were claiming a 10 minute kill time at 20° C. with the AOAC method (J M Ascenzi et al, Surgikos, Res. Div., Oct. 1984). The influence of temperature is appreciated by the data showing 2% alkaline solution (CIDEX) kills *M. tuberculosis* in 70 min. at 20° C., in 30 min. at 25° C., and in only 10 min. at 30° C. U.S. Pat. No. 3,917,850 shows that a mixture of glutaraldehyde and phenol (or phenate salt) in the presence of anionic compounds could display some mycobactericidal synergism.

The new quantitative procedure of J M Ascenzi, T M Wendt, and J W McDowell appears in the Environmental Protection Agency PR Notice 80-1 of May 28, 1986, Section 2, "Tuberculocidal Efficacy Testing". This utilizes a kill curve concept in which a suspension of approximately $10^6$ colony forming units (CFU) of *M. bovis* BCG is added to each ml of disinfectant in tubes held at the appropriate temperature.

Aldehydes have a strong odor and their vapors can be very irritating to mucous membranes. To solve this problem researchers have tried to combine aldehydes with various glycols (U.S. Pat. No. 3,886,269). Through hydrogen bonding, glycols and aldehydes form physical complexes (i.e., larger molecules) which exhibit a lower vapor pressure and less eye and skin irritation. This method was first suggested by Trujillo and Lindell in a paper entitled, "New Formaldehyde Based Disinfectants" (J. Appl. Microb, 26(1):106-110, July 1973). The same year, Harriet Field of the Queen Mary Veteran's Hospital in Montreal, Canada, reported the elimination of noxious glutaraldehyde vapors using propylene glycol and glycerol. The direct complexing of a glutaraldehyde solution with triethyleneglycol was first reported by Boucher in the summer of 1975. On Feb. 15, 1977, the first odorless commercial glutaraldehyde/triethylene glycol composition was approved by the USDA under the trade name AGROCIDE 2. A concentrate of this formula was later registered by the EPA (Feb. 2, 1979) under the Registration No. 15136-5. Between 1976 and 1977, H. D. Muller of the University of Georgia College of Agriculture released several reports describing the successful replacement of formaldehyde by the Boucher glutaraldehyde/triethylene glycol solutions for poultry hatcheries applications (Evaluation of AGROCIDE in a commercial broiler hatchery, Field Trial II, Oct. 20, 1976 by Harry D. Muller, Ext. Poultry Sci, University of Georgia, Athens, Ga.). The use of these triethylene glycol complexes in hospitals was later mentioned by Boucher in November, 1978 (Respiratory Care 23(11):1063-1072). The glutaraldehyde/triethylene glycol solutions of Boucher and Muller were potentiated with TERGITOL 15-S-12 a non-ionic surfactant. The original formula registered by the USDA in early 1977 has been marketed in this country since 1975 under the trade name AGROCIDE, MC25, WAVI-CIDE-06, and 05. In all these formulations the amount of deodorizing triethylene glycol (TEG) was six times higher than the concentration of dialdehyde. In other words, a 0.5% glutaraldehyde formula contained 3% TEG while a 0.25% contained 1.5% TEG.

BRIEF SUMMARY OF THE INVENTION

This invention relates to the development of a family of glutaraldehyde-based surface disinfectants which are extremely efficacious against mycobacteria. To achieve this goal it was necessary to find chemicals which quickly disrupt the protective lipid-rich cell wall of *Mycobacterium tuberculosis* and thus allow a faster penetration of the cidal aldehyde radicals which then interact with nucleic acids. It has been discovered that anionic surfactants of the alkyl sulfate, alkyl sulfonate, alcohol sulfate or alkyl aryl sulfonate type fulfill such a need for a quick lipids cell wall destruction in the presence of glutaraldehyde hydrates and monomers. For example, a preferred anionic surfactant such as sodium dodecyl sulfate (SDS) has been shown to be far superior to solubilize lipid - protein complexes in mycobacterial cell walls than the best non-ionic surfactants currently used in today's glutaraldehyde formulae (see U.S. Pat. Nos. 3,968,248 and 4,436,754). It has also been discovered that adding glycol molecules to deodorize glutaraldehyde solutions (see U.S. Pat. No. 3,886,269) can greatly affect the tuberculocidal activity of glycol/glutaraldehyde mixtures. Mycobactericidal activity appears to be inversely related to the ratio of glycol to aldehydes in a glutaraldehyde formulation.

It is one purpose of the present invention to outline the conditions under which an odorless glutaraldehyde (i.e., complexed with a glycol) could maximize its tuberculocidal activity by adding a suitable anionic surfactant.

It is another purpose of this invention to evaluate tuberculocidal activity of disinfectants using the method approved by the EPA under strict and controlled conditions.

It is another object of this invention to show that glutaraldehyde solutions containing specific anionic surfactants can destroy *M. tuberculosis* on surfaces faster than non-ionic glutaraldehyde formulations.

It is yet another purpose of this invention to assess the influence of the addition of glycols on mycobactericidal activity of glutaraldehyde-anionic compositions when tested with the EPA quantitative procedure.

Still another object of the present invention is to establish the magnitude of the gain, if any, in tuberculocidal activity when substituting non-ionics with anionics in "ready to use" hospital sterilants containing 0.5% to 5% glutaraldehyde.

As will be more fully described hereafter, we have now found that by replacing non-ionics with anionics such as alkyl sulfonates (ARCTIC SYNTEX A—a trademark of the Colgate Co.), alcohol sulfates (DUPONOL WA—a trademark of the DuPont Co.) and alkyl aryl sulfonates (SANTOMERSE 3—a trademark of Monsanto, or ALKANOL B—a trademark of the DuPont Co.), this class of surfactant has mycobactericidal superiority when it was added to glutaraldehyde disinfectant solutions.

Another significant discovery herein lies in the fact that adding glycol molecules to deodorize glutaraldehyde greatly affects the tuberculocidal activity of the glycol/aldehydes solution. Table IV shows results from both anionic and non-ionic glutaraldehyde compositions.

BRIEF DESCRIPTION OF THE DRAWINGS

FIG. 1 shows the rate of kill of *M. bovis* (BCG) by two glutaraldehyde formula containing the same amount of active ingredient but with two different types of surfactants. At equal concentrations, the anionic surfactant displays a faster kill rate. FIG. 2 shows the different kill rates of formula with and without glycol, but with the same amount of glutaraldehyde and surfactant. A ratio of glycol to aldehydes of six slows down considerably the tuberculocidal activity. Results of user samples of glutaraldehyde-containing solutions with various surfactants, ionic and non-ionic and with a glycol-containing substance are shown. These correspond to the numbered samples listed in Tables II and IV. The times in minutes are shown as maximized at 10' in FIG. 1 and at 30' in FIG. 2. Log S/S(O) relates to the plotted tables of averages of survivors divided by the initial count for each time point measured in minutes.

DETAILED DESCRIPTION OF THE INVENTION

Figure 1:
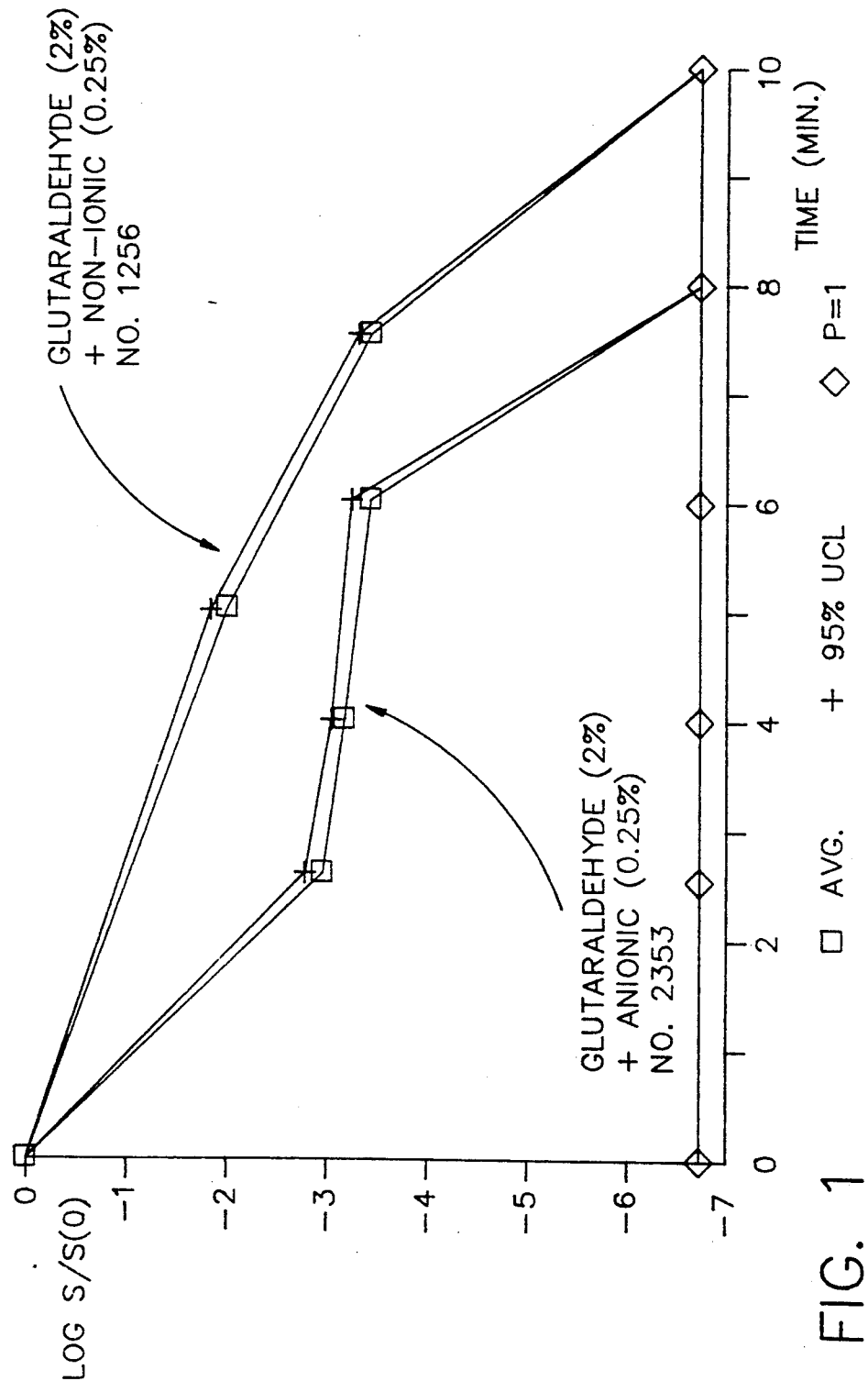
FIGS. 1 and 2 depict the survival rate, that is the level of activity of the *Mycobacteria tuberculosis* organism which is quantitively determined according to the EPA procedures published May 28, 1986.

Electron micrographs of thin sections of *M. tuberculosis* show a thick wall composed of three layers enclosing a plasma membrane that is also a three layered structure. Chemically, the wall of the mycobacterium is very complex and presents many unique characteristics. The most striking feature is its high lipid content (up to 60% of its dry weight) which accounts for most of the unusual properties of this microorganism: (a) relative impermeability to stains, (b) acid fastness, and (c) unusual resistance to killing by acid or alkali. The backbone of the mycobacterial cell wall is a covalent structure consisting of two polymers covalently linked by phosphodiester bonds, a peptidoglycan and an arabinogalactan. As much as 70 percent of the cross linking in the peptidoglycan consists of interpeptide bridges between molecules of mesodiaminopimelic acid (DPA). A large number of other compounds are also associated with the mycolate-arabinogalactan-peptidoglycan complex. Crude cell wall preparations contain large amounts of amino acids which are said to be present in the wall as lipoproteins or glycolipoproteins. In addition to the glycolipids bound to the peptidoglycan, other lipid substances are present on the cell surface: cord factor (trehalose 6, 6'-dimycolate), sulfatides and mycosides all of which are important from the biological activity viewpoint.

The acid-fastness characteristic of the tubercle bacillus is related to its lipid content. It is believed that the acid-fastness of mycobacteria is based on a lipid-barrier principle, in which an increased hydrophobicity of the surface layers follows the complexing of dye with mycolic acid residues that are present in the cell wall. This prevents exit of carbolfuchsin that has become trapped in the interior of the cell.

It is believed that fast cidal reaction depends on the penetration of aldehydes radicals through the protective cell wall layers.

Anionic compounds are the most likely surface active agents which could help penetrate the lipid barrier and solubilize cell membranes in the form of surfactant-lipid-protein complexes. The surfactant-lipid-protein complexes are further solubilized to provide surfactant-protein complexes and surfactant-lipid complexes. Another advantage of the use of an anionic agent, for instance sodium dodecyl sulfate (SDS), is it strong denaturant activity which dissociates proteins into polypeptide chains. The prior art of the effects of SDS (2% W/V) was conducted by A D Russell, et al, (Int. Symp. Resist Microorg. to Disinfectants, Oct, 1973, Poznan, Poland) which showed that at 35° C. whole cells and cell walls of $E.$ $coli$ were disintegrated in a few minutes due to the extraction of lipoproteins from the walls. Pre-treatment of cells and walls of $E.$ $coli$ with glutaraldehyde greatly reduced subsequent SDS lysis and the protective effect of glutaraldehyde was greater with cells than with cell walls. No data appears with a mixture of glutaraldehyde with SDS to assess the influence of such a binary composition.

It is believed that the presence of SDS in a glutaraldehyde solution will facilitate the destruction of the protective lipid layers and, therefore, will allow a faster penetration and reaction of the cidal glutaraldehyde monomers. The main cidal agents in glutaraldehyde solutions seem to be the end aldehydes of the glutaraldehyde monomers. Apparently, these aldehydes react at different levels in the mycobacteria. Since glutaraldehyde is an alkylating agent it may react chemically with sulfhydryl, hydroxyl, amino and carboxyl groups of proteins (Hoffman R K, Inhibition and Destruction of the Microbial Cell, Acad Press, London/New York, pp. 225-258, 1941). Glutaraldehyde has also been shown to react with amino groups in nucleic acids where it produces alterations in the arrangement of the DNA and subsequently alters protein synthesis (Sangar et al, Journal of Gen. Virology, 21: 399-406, 1973). Although the peptidoglycan of mycobacteria is not identical to the peptidoglycan chain of $B.$ $subtilis$ spores, (Hughes R C and Thurman P F, Biochem J, 119: p. 925, 1970) approximately 30 to 50% of the available-$NH_2$ groups in isolated $B.$ $subtilis$ spore coats can react with glutaraldehyde thus promoting chain cross-linking. There are many potential sites in a mycobacterium for dialdehydes reaction. However, for fast inactivation of $M.$ $tuberculosis$, one needs a quick solubilization of the multilayer lipid wall allowing penetration of cidal entities to critical sites. To achieve this solubilization it is well known that one cannot use cationic surfactants (B D Davis, Microbiology, Mycobacteria, Chapter 37,, P. 727, Harper and Row, New York, 1980 ed). Non-ionic surfactants of the polyoxyethylene type such as TRITON X-100 (a trademark of the Rohm and Haas Company) and TERGITOL[1] 15-S-12 have been used in the past but with limited success.

[1]Tergitol is a trademark of the Union Carbide Chemical Company for non-ionic, biodegradable intermediates comprising ethoxylates and ethoxylates of linear secondary alcohols. The formula for 15-S-12 appears on page 14.

We have now found that the complexing of triethylene glycol, when tested at any amounts six times higher than the glutaraldehyde concentration, results in a substantial decrease in tuberculocidal activity. The survival curves shown hereafter show that by using glutaraldehyde solutions containing some glycol "lag time" appears (around 15 minutes) before a substantial mycobactericidal kill is observed. It is believed that triethyleneglycol molecules may first combine with aldehyde monomers to form physical complexes. This initial step (during the first fifteen minutes) decreases the number of active aldehydes available to diffuse and react at critical sites with the microorganisms. The formation of larger molecular complexes may slow down the penetration of aldehyde monomers through the lipid barrier. To reduce the slowdown in cidal activity due to the presence of glycol complexes, the glycol concentration in the glutaraldehyde formula could be decreased. Key components of the present invention include deodorizing, as well as decreasing mucous membrane irritation and potential metals corrosion. As seen from the data in Table V, a compromise was necessary to achieve high tuberculocidal activity in an odorless solution. Two solutions with a low glutaraldehyde content (0.5%) and with the same amount (0.0625%) of surfactant are evaluated. Only the ratio of glycol to glutaraldehyde varied (G/A) from 0 to 6. In both cases, the mycobactericidal efficacy of the solutions rapidly decrease when the G/A ratio is greater than 2. As expected, in the region (G/A≅1.2) where tuberculocidal activity is maximum, the glutaraldehyde/anionic formulation is superior to the glutaraldehyde/non-ionic composition. Low glutaraldehyde concentrations (below 0.5% W/V) do not create serious odor or corrosion problems. In determining the absence of odor, trained laboratory personnel with normal olfactory senses rated and observed the atmosphere and environment in a 60 cubic meter room containing an open, flat container with one gallon of product. This closed room had no ventilation. The solution remained at least 24 hours in the flat glass container. The 0.5% glutaraldehyde/surfactant solution shows a mean primary irritation score of 0.33, which is one of the lowest ratings defined as "minimally irritating". Even the more sensitive rabbit eye tests shows that 0.5% glutaraldehyde is at the threshold for induction of inflammatory effects. One achieves high tuberculocidal efficacy (i.e., less than 10 min. at 20° C.), little odor, and practically no corrosion by using an aqueous glutaraldehyde (0.5%) anionic (0.062%) formulation. However, other needs such as sporicidal activity require higher concentration of glutaraldehyde. The best odorless composition incorporates a glycol with a G/A ratio smaller than two. The lower the G/A ratio, the greater the mycobactericidal activity.

EXAMPLES

All the tests described in the present application were conducted at 20° C., the temperature recommended in the old AOAC method. After exposure of the bacteria to the test disinfectant for varying time intervals, aliquots of the disinfectant are removed and added to an equivalent volume of a neutralizing solution (in our studies it was 0.5% sodium metabisulfite). Each tube of neutralized disinfectant containing mycobacteria is then diluted. Counts of viable bacteria are made from each dilution using a membrane filter (0.45 microns pore size) technique. Membrane filters with mycobacteria are placed on Mycobacteria 7H11 agar. Each disinfectant is plated in quintuplicate. Incubation takes place at 37° C. for 21 days. Colonies growing up on membranes are then counted under a high power optical microscope. All the data are set up in tables of averages and plotted as average survivors divided by initial count (S/So) for each time point. The plots are made on semi-log paper for easier interpretation and comparisons.

To eliminate the influence of pH, all solutions are buffered in the 6 to 7.4 range and preferably at between 5.90 to 6.32 with a mixture of monobasic potassium phosphate and anhydrous dibasic sodium phosphate. The active ingredient is the glutaraldehyde monomer which is in equilibrium with reversible polymers (R. M. G. Boucher, Proc West Pharmacol. Soc. 16:282-288, 1973) when operating in the acid range. The glutaraldehyde content is given in the first column and varied from 0 to 2% (W/V). The glutaraldehyde is assayed using the hydroxylamine hydrochloride method (Union Carbide, BB-TL-2003, 1986).

Two types of surfactants are shown: non-ionic and anionic. These two types of surface active agents are widely used in disinfectant formula due to their specific actions on key components of microorganisms (proteins, enzymes, and membranes). In the case of proteins, non-ionic surfactants show either no interaction or extremely weak interactions, while anionics show intense interaction with proteins and polymers. Usually, anionics solubilize the protective lipid layers of mycobacteria which would not be affected by non-ionics. Non-ionic surfactants generally do not inactivate or denaturate enzymes, while anionics would be expected to affect enzyme activity.

As a typical non-ionic surfactant, TERGITOL 15-S-12 which has been successfully used in acid glutaraldehyde sterilant formula (U.S. Pat. No. 3,968,248) under the trade names SONACIDE, WAVICIDE, STERALL, and BANICIDE is evaluated. It is an ethoxylate of isomeric linear alcohols whose structural formula can be written as follows:

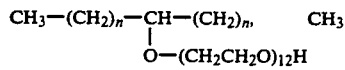

Where (n + n,) = 8-12

The total number of carbon atoms on the hydrophobic portion of the molecule is in the 11 to 15 range. This compound is very stable and it is widely used in industry to promote bleaching, dyeing, finishing, solvent scouring, etc. Due to its low foam characteristics and wetting properties, this surfactant has been used in many dishwasher cleaning liquids.

As a typical anionic surfactant, we use the molecule of sodium dodecyl sulfate (SDS) which is negatively charged. The structural molecular formula can be written as follows:

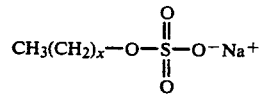

Hydrophilic segment with x = 11

Sodium dodecyl sulfate has often been used in the past as an additive in phenolic-based disinfectant formula. The amount of surfactant added in our glutaraldehyde solutions is always computed on the basis of one to eight because it is the ratio successfully used in commercial sterilants of the WAVICIDE type. In other words, a 2% glutaraldehyde solution will contain 0.25% (W/V) anionic or non-ionic surfactant, while a 0.5% glutaraldehyde will contain 0.062% surfactant. The same rule applied for the glycol/glutaraldehyde solutions evaluated in Table IV.

The percentage of surfactant is indicated between parenthesis in the composition column when non-ionic or anionic surfactants are tested in the absence of glutaraldehyde. To cover the influence of aging on the various glutaraldehyde solutions, some tests are also conducted with compositions as old as eleven months.

In Table II, the mycobacteria survival curves for samples 1144 and 1143 showed very little difference. This suggests that the non-ionic surfactant does not contribute greatly to the penetration of the reactive cidal aldehydes. However, all other things being equal, if one replaces the non-ionic with an anionic surfactant, the M. bovis (BCG) kill time is always shorter. It is reduced by 33% with a 0.5% (W/V) glutaraldehyde formula and by 20% when experimenting the 2% (W/V) concentrate (see FIG. 1). Aqueous non-ionic glutaraldehyde formula (i.e., without glycol) gives the same results (a 15 minute kill time at 20° C.) for a two or eleven month old solutions. As expected, when acting alone, surfactants exhibited no tuberculocidal action at the concentration used in our experiments. The same increase in cidal activity was previously observed (see R. Boucher, U.S. patent appl. Ser. No. 07/286,738, Dec. 20, 1988) when replacing non-ionics by anionics in virucidal glutaraldehyde formulations. Table III shows, for instance, the data pertaining to a lipophilic virus such as Herpes Simplex and to a more resistant Coxsackie virus B6. Although there is some similarity in the virucidal and mycobactericidal behavior of surfactant/glutaraldehyde formula, it is impossible to predict mycobactericidal efficacy from data collected with viruses. The resistance of *M. tuberculosis* to disinfectants is several orders of magnitude higher than that observed with Coxsackie virus. The percentage of glycol is indicated between parentheses in the composition column of Tables II and IV when triethylene glycol is tested in the absence of glutaraldehyde. To cover the influence of aging on the various glutaraldehyde/glycol formula, some tests were conducted with compositions as old as 14 months. All the tests in Table IV were performed at 20°C. with the EPA quantitative method. All tests were conducted with solutions buffered in the 6. to 6.3 pH range.

Data in Table II show that the presence or absence of non-ionic surfactants does not seem to influence the tuberculocidal efficacy of aqueous glutaraldehyde solutions. The same phenomenon was observed with glycol/glutaraldehyde compositions (samples 0215 and 1784). However, contrary to results obtained with aqueous glycolless solutions, the presence of anionics (1403 and 1417) did not increase the tuberculocidal efficacy under these conditions.

Figure 2:
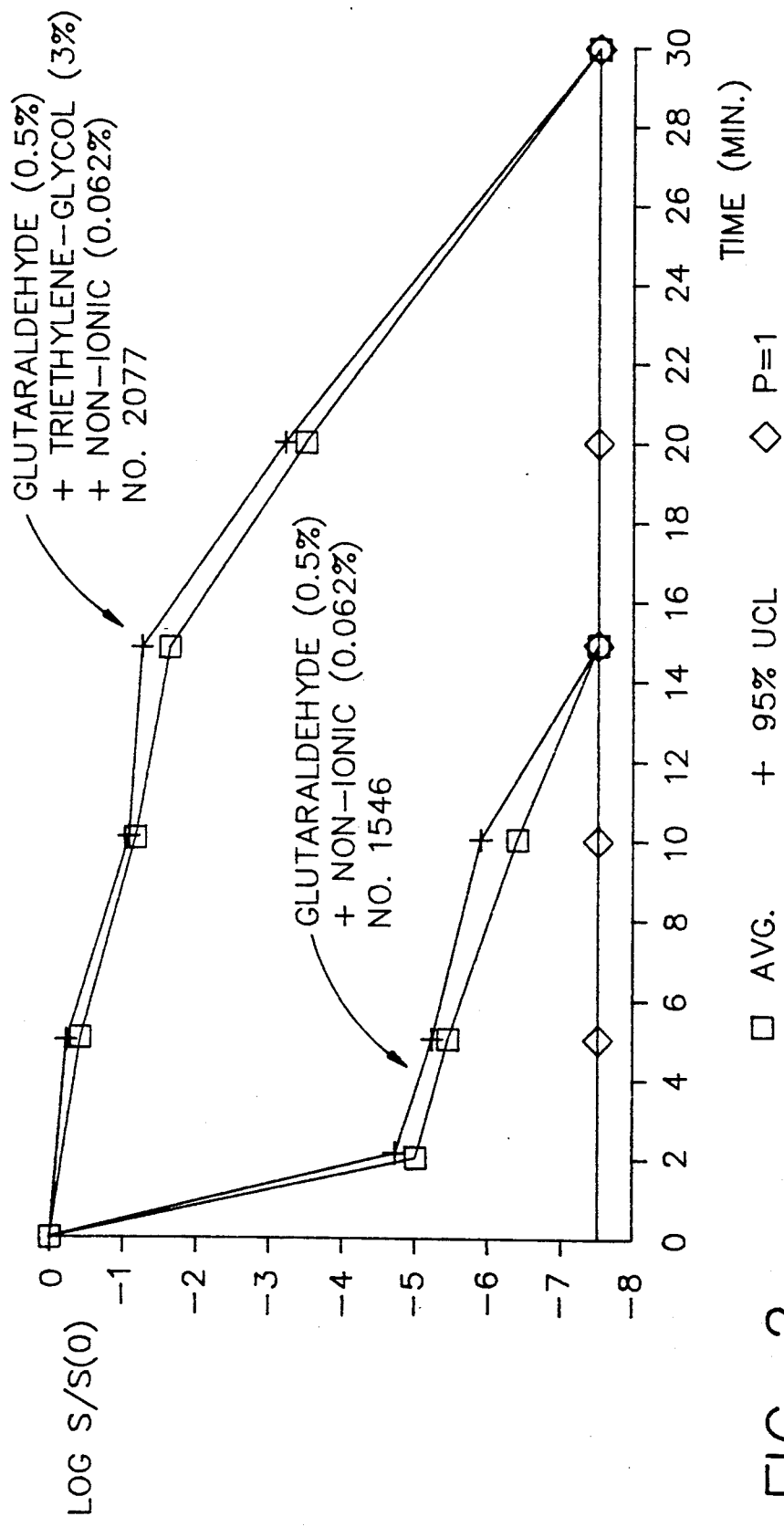

Mycobactericidal activity of nine month old samples (0217) was comparable to that of two month old solutions (1403 and 1417). However, as expected, 14 month old samples showed a strong yellowing of the solution and took a longer time (40 min.) to kill *M. tuberculosis*. Tests were also conducted with sample 2077, which contained the same amount of glutaraldehyde and non-ionics as the glycolless samples 1144 and 1546. As can be seen from the survival curve (FIG. 2), the presence of triethylene glycol doubled the tuberculocidal time. Similar tests with anionic solutions containing the same 0.5% glutaraldehyde content (1145 and 2355) increased the tuberculocidal time from 10 to 30 minutes in the presence of glycol.

In the prior art, meaningful increases in cidal activity were only observed with large amounts of phenols (at least 1.7%) in the presence of 2.5% glutaraldehyde. Such a large concentration of phenol not only causes a strong odor, but also increases the glutaraldehyde odor due to increasing the glutaraldehyde vaporization (see U.S. Pat. No. 4,436,754). The influence of phenol on the present glutaraldehyde-glycol formula containing two different surfactants are assessed in test samples No. 2078 and 2079 in Table IV which show an entirely negative influence of the phenol under our experimental conditions.

The manufacture of mycobactericidal solutions containing the three following chemicals: aqueous glutaraldehyde, triethylene glycol (TEG) and sodium dodecylsulfate (SDS) is extremely easy since both TEG and SDS dissolve in a matter of minutes into an aqueous solution of acid glutaraldehyde under mild agitating conditions at room temperature. Other substances may be added to the novel tuberculocidal compositions object of the present invention provided they have no detrimental effect on the mycobactericidal activity of the solutions. For instance, small amounts of ethylenediaminetetraacetic (EDTA) salts or lysozyme could be added to accelerate destabilization of the lipid and peptidoglycan protective layers. Other salts such as sodium gluconate could also be added to neutralize calcium precipitation during formula dilution with hard water. Anti-foaming agents such as organic silicone compounds, anticorrosive agents such as sodium nitrite, dyes or fragrances to improve commercial appeal could also be added as long as they do not adversely affect the cidal mechanisms.

Although several specific examples of the inventive concept have been described for purposes of illustration, the invention should not be construed as limited thereby, nor to the specific features mentioned therein except as the same may be included in the claims appended hereto. It is also understood that changes, modifications, and variations may be made without departing from the spirit and scope of the present invention.

For instance, knowing the excellent mycobactericidal characteristics of alcoholic solutions, lower alkanols such as methanol, ethanol, isopropanol, and the like could be used as the solvent rather than filtered deionized water. A mixture of both could also be used. These minor modifications in the composition of the solvent will be dictated by the nature of the applications: decontamination of instruments, inanimate or animate surfaces, skin degerming, wound cleaning, etc.

TABLE 1

Numbers of *M. Bovis* BCG Organisms Surviving after Exposure to Fresh Glutaraldehyde-Based Disinfectants at 20° C. for Varying Time Periods

| Time (min) | CIDEX Solution | CIDEX FORMULA 7 Solution | Sporicidin | Sonacide | Steril-Ize | Glutarex | Omnicide |
|---|---|---|---|---|---|---|---|
| 0 | $4.02 \times 10^5$ | $4.47 \times 10^5$ | $4.47 \times 10^5$ | $4.47 \times 10^5$ | $4.47 \times 10^5$ | $4.47 \times 10^5$ | $4.47 \times 10^5$ |
| 1 | $3.90 \times 10^4$ | $5.30 \times 10^4$ | $3.58 \times 10^5$ | $3.42 \times 10^5$ | $5.85 \times 10^4$ | $5.35 \times 10^4$ | $6.75 \times 10^4$ |
| 2 | $2.28 \times 10^4$ | $5.35 \times 10^4$ | $2.77 \times 10^5$ | $3.50 \times 10^5$ | $2.98 \times 10^4$ | $5.30 \times 10^4$ | $4.90 \times 10^4$ |
| 5 | $1.80 \times 10^4$ | $4.00 \times 10^4$ | $1.26 \times 10^5$ | $2.27 \times 10^5$ | $2.40 \times 10^4$ | $3.70 \times 10^4$ | $3.96 \times 10^4$ |
| 10 | $9.80 \times 10^3$ | $2.07 \times 10^4$ | $6.30 \times 10^4$ | $1.10 \times 10^5$ | $7.30 \times 10^3$ | $2.16 \times 10^4$ | $1.51 \times 10^4$ |
| 20 | $1.01 \times 10^3$ | $6.67 \times 10^3$ | $3.96 \times 10^4$ | $1.02 \times 10^4$ | $2.53 \times 10^2$ | $7.86 \times 10^3$ | $3.91 \times 10^3$ |

Reproduced from Page 3 of the paper by J. M. Ascenzi, T. M. Wendt, and J. W. McDowell Entitled, "Important Information Concerning the Reuse of Glutaraldehyde-Based Disinfectants and their Tuberculocidal Activity", published by Research Division, Surgikos, Inc., October 1984.

The above trademarked products and registered owners are:

CIDEX and CIDEX 7 Surgikos (a Johnson and Johnson company)

SPORICIDIN - Sporicidin Co. of Washington. D.C.

SONACIDE - Ayerst Lab (an American home products company)

GLUTAREX - 3M Company of Minnesota

STERIL-IZE - Larson Labs, Inc., Erie, PA

OMNICIDE - ADM Medical Division, Missoula, MT

TABLE II

Mycobactericidal tests of mycobacterium tuberculosis (TB) conducted with the EPA quantitative procedure PR notice 80-1, May 28, 1986.

| Sample | Composition | Glutaraldehyde Concentration | TB Killing Time | Solutions PH | Age |
|---|---|---|---|---|---|
| 1546 and 1144 | Glut + non-ionic | 0.5% | 15 min. | 5.9–6.32 | 11 and 2 months |
| 1143 | Glut | 0.5% | 15 min. | 6.30 | 2 months |
| 1145 | Glut + anionic | 0.5% | 10 min. | 6.40 | 2 months |
| 1147 | Anionic (0.062%) | 0.0% | No Kill | 6.35 | 2 months |
| 1150 | Non-ionic (0.062%) | 0.0% | No Kill | 6.38 | 2 months |
| 1255 | Glut + non-ionic | 2.0% | 10 min. | 6.30 | 2½ months |
| 1256 | Glut + non-ionic | 2.0% | 10 min. | 6.30 | 2½ months |
| 2353 | Glut + anionic | 2.0% | 8 min. | 6.29 | 1 month |

Glut = glutaraldehyde
The surfactants mentioned in Tables II, III, and IV are the sodium dodecyl sulfate (anionic) described in Page 15 and the ethoxylate of isomeric linear alcohols (non-ionic) described on Page 14.

TABLE III

Inactivation Study* of Two Viruses with Surfactant/Glutaraldehyde Formula

| | % Viral Activity Remaining after 10 Minutes Exposure | Type of Virus Tested |
|---|---|---|
| Glutaraldehyde (0.006%) + non-ionic (0.05%) | 100% | Coxsackie Virus B6 (CBV) |
| Glutaraldehyde (0.006%) + anionic (0.05%) | 40% | Coxsackie Virus B6 (CBV) |
| Glutaraldehyde (0.0025%) + non-ionic (0.0005%) | 50% | Herpes Simplex Virus Type I (HSV) |
| Glutaraldehyde (0.0025%) + anionic (0.0005%) | 32% | Herpes Simplex Virus Type I (HSV) |

*Virucidal tests conducted according to EPA notice DIS/TSS-7, November 12, 1981

TABLE IV

Mycobacterial tests conducted with the EPA quantitative procedure PR notice 80-1, May 28, 1986.

| Sample | Composition | Glutaraldehyde Concentration | TB Killing Time | Solutions PH | Age |
|---|---|---|---|---|---|
| 0.148 and 0215 | Glut + TEG + non-ionic | 0.25% | 30 min. | 6.13–6.00 | 6 months |
| 1788 | Glut + TEG + non-ionic | 0.25% | 30 min. | 6.22 | 3 months |
| 1784 | Glut + TEG | 0.25% | 30 min. | 6.20 | 3 months |
| 1362 | TEG (1.5%) + non-ionic (0.031%) | 0.00% | No Kill | 6.34 | 3 months |
| 1257 | Glut + TEG + anionic | 0.25% | 40 min. | 6.35 | 14 months |
| 0217 | Glut + TEG + anionic | 0.25% | 30 min. | 5.97 | 9 months |
| 1403 and 1417 | Glut + TEG + anionic | 0.25% | 30 min. | 6.25–6.31 | 2 months |
| 1361 and 1792 | TEG (1.5%) + anionic (0.031%) | 0.00% | No Kill | 6.32–6.28 | 2 months |
| 2077 | Glut + TEG + non-ionic | 0.50% | 30 min. | 5.90 | 2 months |
| 2355 | Glut + TEG + anionic | 0.50% | 30 min. | 6.04 | 1 month |
| 2080 | TEG (3%) + anionic (0.062%) | 0.00% | No Kill | 6.31 | 2 months |
| 2078 | Glut + TEG + non-ionic + Phenol (0.5%) | 0.50% | 60 min. | 6.07 | 2 months |
| 2079 | Glut + TEG + anionic + Phenol (0.5%) | 0.50% | No Kill | 6.31 | 2 months |

Glut = glutaraldehyde
TEG = triethylene glycol
TB = mycobacterium bacillus

TABLE V

INFLUENCE OF GLYCOL/ALDEHYDE RATIO (G/A) ON MYCOBACTERICIDAL ACTIVITY OF MYCOBACTERIUM TUBERCULOSIS (TB)

(a) Glutaraldehyde (0.5%) + anionic (0.0625%) solution.

| G/A | 0 | 0.1 | 0.25 | 0.75 | 1 | 1.2 | 2 | 6 |
|---|---|---|---|---|---|---|---|---|
| Triethylene Glycol Percent (W/V) | None | 0.05 | 0.125 | 0.375 | 0.5 | 0.6 | 1 | 3 |
| Odor Control* | – | + | + | + | + | + | + | + |
| TB Killing Time in Min. | 10 | 10 | 15 | 15 | 20 | 20 to 30 | 30 to 40 | 30 to 40 |

(b) Glutaraldehyde (0.5%) + non-ionic (0.0625%) solution

| G/A | 0 | 0.1 | 0.25 | 0.75 | 1 | 1.2 | 2 | 6 |
|---|---|---|---|---|---|---|---|---|
| Triethylene Glycol Percent (W/V) | None | 0.05 | 0.125 | 0.375 | 0.5 | 0.6 | 1 | 3 |
| Odor Control* | – | + | + | + | + | + | + | + |
| TB Killing Time in Min. | 15 | 15 | 20 | 20 | 30 | 30 to 40 | 30 to 40 | 30 to 40 |

*A 0.5% glutaraldehyde level is the threshold for odor control.

What is claimed is:

1. The method of destroying mycobacteria on an animate or inanimate surface which comprises applying an effective amount of a tuberculocidal solution free of both phenol and non-ionic surfactant to said surface wherein said solution comprises:

(a) a solvent consisting of water or a lower alkanol;

(b) between about 0.1 to about 16% by weight of a dialdehyde containing from 2 to about 6 carbons atoms;

(c) an odor-reducing agent selected from the group consisting of ethylene glycol, propylene glycol, diethylene glycol, triethylene glycol, polyethylene glycol, polypropylene glycol and mixtures thereof;

(d) between about 0.02 to about 10 percent by weight of an anionic surfactant having a negatively-charged hydrophilic moiety selected from the group consisting of alkyl sulfates, alkyl sulfonates, alcohol sulfates, alkyl aryl sulfonates, dialkyl sulfosuccinates, and mixtures thereof;

(e) buffer salts in sufficient amounts to stabilize the pH of the solution inside the range of from about 6 to 7.4; and further wherein the glycol compounds are present in a ratio of 0.1 to 6.0 as compared to the dialdehyde.

2. The method of claim 1 wherein said dialdehyde is glutaraldehyde.

3. The method of claim 1 wherein said odor-reducing agent is triethylene glycol.

4. The method of claim 1 wherein said anionic surfactant is sodium dodecylsulfate.

5. The method of claim 1 wherein said anionic surfactant is a dialkyl sulfosuccinate.

6. The method of claim 1 wherein the buffer salt is selected from the group consisting of alkali metal carbonates, bicarbonates, phosphates and borates, organic carboxylate salts, and mixtures thereof.

7. The method of claim 1 wherein said composition has a pH range of from 5.9 to about 6.32 effected by a mixture of monobasic potassium or sodium phosphate and anhydrous dibasic sodium phosphate.

8. The method of claim 1 which comprises applying said composition to an inanimate surface contaminated by mycobacteria.

9. The method of claim 1 which comprises destroying mycobacteria by scrubbing contaminated skin with said composition.

10. The method of claim 9 wherein said composition comprises between about 0.25% to about 2% glutaraldehyde, about 0.031% to about 0.25% anionic surfactant and a glycol to glutaraldehyde ratio smaller than two.

11. The method of claim 1 which comprises cleansing a mycobacteria contaminated wound by applying thereto said composition.

12. The method of claim 11 wherein said composition comprises between about 0.25% to about 2% glutaraldehyde, about 0.031% to about 0.25% anionic surfactant and a glycol to glutaraldehyde ratio smaller than two.

13. The method of claim 1 wherein said composition comprises between about 0.25% to about 2% glutaraldehyde, about 0.031% to about 0.25% anionic surfactant and a glycol to glutaraldehyde ratio smaller than two.

14. The method of claim 1 wherein said composition comprises between about 0.25% to about 2% glutaraldehyde, about 0.031% to about 0.25% anionic surfactant and a glycol to glutaraldehyde ratio smaller than two.

15. The method of destroying mycobacteria on an animate or inanimate surface which comprises applying an effective amount of a tuberculocidal solution to said surface wherein said solution consists essentially of:

(a) a solvent consisting of water or a lower alkanol;

(b) between about 0.1 to about 16% by weight of a dialdehyde containing from 2 to about 6 carbons atoms;

(c) an odor-reducing agent selected from the group consisting of ethylene glycol, propylene glycol, diethylene glycol, triethylene glycol, polyethylene glycol, polypropylene glycol, and mixtures thereof;

(d) between about 0.02 to about 10 percent by weight of an anionic surfactant having a negatively-charged hydrophilic moiety selected from the group consisting of alkyl sulfates, alkyl sulfonates, alcohol sulfates, alkyl aryl sulfonates, dialkyl sulfosuccinates, and mixtures thereof;

(e) buffer salts in sufficient amounts to stabilize the pH of the solution inside the range of from about 6 to 7.4; and further wherein the glycol compounds are present in a ratio of 0.1 to 6.0 as compared to the dialdehyde.

16. The method of claim 15 which comprises destroying mycobacteria by scrubbing contaminated skin with said composition.

17. The method of claim 15 wherein said dialdehyde is glutaraldehyde.

18. The method of claim 15 wherein said odor-reducing agent is triethylene glycol.

19. The method of claim 15 wherein said anionic surfactant is a dialkyl sulfosuccinate.

20. The method of claim 16 wherein said composition comprises between about 0.25% to about 2% glutaraldehyde, about 0.031% to about 0.25% anionic surfactant and a glycol to glutaraldehyde ratio smaller than two.

* * * * *